(12) United States Patent
Rome et al.

(10) Patent No.: US 7,094,218 B2
(45) Date of Patent: Aug. 22, 2006

(54) VALVED CATHETER

(75) Inventors: Guy Rome, West Valley, UT (US); William R. Barron, Riverton, UT (US); Bret Hamatake, Grantsville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 94 days.

(21) Appl. No.: 10/803,207

(22) Filed: Mar. 18, 2004

(65) Prior Publication Data

US 2005/0209572 A1 Sep. 22, 2005

(51) Int. Cl.
*A61M 29/00* (2006.01)
*A61M 5/14* (2006.01)

(52) U.S. Cl. .................... 604/99.04; 604/256

(58) Field of Classification Search ............... 604/319, 604/99.02, 99.04, 256
See application file for complete search history.

(56) References Cited

U.S. PATENT DOCUMENTS

| | | | |
|---|---|---|---|
| 3,176,690 A | 4/1965 | H'Doubler | |
| D217,795 S | 6/1970 | Spaven | |
| 3,805,794 A | 4/1974 | Schlesigner | |
| 4,000,739 A | 1/1977 | Stevens | |
| 4,068,659 A | 1/1978 | Moorehead | |
| 4,198,973 A | 4/1980 | Millet | |
| 4,233,974 A | 11/1980 | Desecki et al. | |
| 4,235,232 A * | 11/1980 | Spaven et al. | 604/178 |
| 4,296,747 A | 10/1981 | Ogle | |
| 4,306,562 A | 12/1981 | Osborne | |
| 4,411,654 A | 10/1983 | Boarini et al. | |
| 4,412,832 A | 11/1983 | Kling et al. | |
| 4,424,833 A | 1/1984 | Spector et al. | |
| 4,430,081 A | 2/1984 | Timmermans | |
| 4,431,426 A | 2/1984 | Groshong et al. | |
| 4,436,519 A | 3/1984 | O'Neill | |
| 4,439,179 A * | 3/1984 | Lueders et al. | 604/34 |
| 4,445,893 A | 5/1984 | Bodicky | |
| 4,449,973 A | 5/1984 | Luther | |
| 4,468,224 A | 8/1984 | Enzmann et al. | |
| 4,473,067 A | 9/1984 | Schiff | |
| RE31,855 E | 3/1985 | Osborne | |
| 4,557,261 A | 12/1985 | Riigheimer | |
| 4,571,241 A | 2/1986 | Christopher | |
| 4,581,012 A | 4/1986 | Brown et al. | |
| 4,581,025 A | 4/1986 | Timmermans | |
| 4,591,355 A | 5/1986 | Hilse | |
| 4,596,559 A | 6/1986 | Fleischhacker | |
| 4,610,665 A | 9/1986 | Matsumoto et al. | |

(Continued)

FOREIGN PATENT DOCUMENTS

EP 1 240 916 A1 9/2002

(Continued)

OTHER PUBLICATIONS

Camp, L. Dawn, "Care of the Groshong Catheter", Oncol. Nurs. Forum, pp. 745-749, vol. 15, No. 6, 1988.*

(Continued)

*Primary Examiner*—Tatyana Zalukaeva
*Assistant Examiner*—Paula L. Craig
(74) *Attorney, Agent, or Firm*—Morrison & Foerster LLP

(57) ABSTRACT

A valved catheter that allows placement and withdrawal of an accessing device or attachable unit without the risk of air embolism or blood loss. The valved catheter includes a catheter tube having a necked portion in its proximal end that forms an integral valve, the necked portion being surrounded by a compression sleeve that biases the valve in a closed position.

20 Claims, 2 Drawing Sheets

U.S. PATENT DOCUMENTS

| | | | |
|---|---|---|---|
| 4,619,643 A | 10/1986 | Bai | |
| 4,626,245 A | 12/1986 | Weinstein | |
| 4,650,472 A | 3/1987 | Bates | |
| 4,673,393 A | 6/1987 | Suzuki et al. | |
| 4,701,159 A | 10/1987 | Brown et al. | |
| 4,722,725 A | 2/1988 | Sawyer et al. | |
| 4,723,550 A | 2/1988 | Bales et al. | |
| 4,726,374 A | 2/1988 | Bales et al. | |
| 4,743,265 A | 5/1988 | Whitehouse et al. | |
| 4,747,833 A | 5/1988 | Kousai et al. | |
| 4,753,765 A | 6/1988 | Pande | |
| 4,772,266 A | 9/1988 | Groshong | |
| 4,784,644 A | 11/1988 | Sawyer et al. | |
| 4,795,426 A | 1/1989 | Jones | |
| 4,798,594 A | 1/1989 | Hillstead | |
| 4,842,592 A | 6/1989 | Caggiani et al. | |
| 4,865,593 A | 9/1989 | Ogawa et al. | |
| 4,909,798 A | 3/1990 | Fleischhacker et al. | |
| 4,921,479 A | 5/1990 | Grayzel | |
| 4,929,235 A | 5/1990 | Merry et al. | |
| 4,929,236 A | 5/1990 | Sampson | |
| 4,932,633 A | 6/1990 | Johnson et al. | |
| 4,935,010 A | 6/1990 | Cox et al. | |
| 4,936,826 A | 6/1990 | Amarasinghe | |
| 4,946,133 A | 8/1990 | Johnson et al. | |
| 4,946,449 A * | 8/1990 | Davis, Jr. | 604/256 |
| 4,952,359 A | 8/1990 | Wells | |
| 4,960,412 A | 10/1990 | Fink | |
| 4,966,588 A | 10/1990 | Rayman et al. | |
| 4,983,168 A | 1/1991 | Moorehead | |
| 4,997,424 A | 3/1991 | Little | |
| 5,007,901 A | 4/1991 | Shields | |
| 5,035,686 A | 7/1991 | Crittenden et al. | |
| 5,041,095 A | 8/1991 | Littrell | |
| 5,053,014 A | 10/1991 | Van Heugten | |
| 5,064,414 A | 11/1991 | Revane | |
| 5,066,285 A | 11/1991 | Hillstead | |
| 5,071,411 A | 12/1991 | Hillstead | |
| 5,078,688 A | 1/1992 | Lobodzinski et al. | |
| 5,085,645 A | 2/1992 | Purdy et al. | |
| 5,092,857 A | 3/1992 | Fleischhacker | |
| 5,098,392 A | 3/1992 | Fleischhacker et al. | |
| 5,098,393 A | 3/1992 | Amplatz et al. | |
| 5,112,301 A | 5/1992 | Fenton, Jr. et al. | |
| 5,114,408 A | 5/1992 | Fleischhaker et al. | |
| 5,117,836 A | 6/1992 | Millar | |
| 5,125,904 A | 6/1992 | Lee | |
| 5,141,497 A | 8/1992 | Erskine | |
| 5,149,327 A | 9/1992 | Oshiyama | |
| 5,154,701 A | 10/1992 | Cheer et al. | |
| 5,158,545 A * | 10/1992 | Trudell et al. | 604/509 |
| 5,160,323 A | 11/1992 | Andrew | |
| 5,163,903 A | 11/1992 | Crittenden et al. | |
| 5,167,634 A | 12/1992 | Corrigan, Jr. et al. | |
| 5,167,637 A | 12/1992 | Okada et al. | |
| 5,169,393 A | 12/1992 | Moorehead et al. | |
| 5,171,222 A | 12/1992 | Euteneuer et al. | |
| 5,180,372 A | 1/1993 | Vegoe et al. | |
| 5,190,529 A | 3/1993 | McCrory et al. | |
| 5,191,898 A | 3/1993 | Millar | |
| 5,197,976 A | 3/1993 | Herweck et al. | |
| 5,201,722 A | 4/1993 | Moorehead et al. | |
| 5,205,834 A | 4/1993 | Moorehead et al. | |
| 5,211,633 A | 5/1993 | Stouder, Jr. | |
| 5,215,538 A | 6/1993 | Larkin | |
| 5,221,263 A | 6/1993 | Sinko et al. | |
| 5,234,410 A | 8/1993 | Graham et al. | |
| 5,242,413 A | 9/1993 | Heiliger | |
| 5,242,430 A | 9/1993 | Arenas et al. | |
| 5,250,033 A | 10/1993 | Evans et al. | |
| 5,255,691 A | 10/1993 | Otten | |
| 5,273,540 A | 12/1993 | Luther et al. | |
| 5,273,546 A | 12/1993 | McLaughlin et al. | |
| 5,275,583 A | 1/1994 | Crainich | |
| 5,279,597 A * | 1/1994 | Dassa et al. | 604/535 |
| 5,290,294 A | 3/1994 | Cox et al. | |
| 5,304,142 A | 4/1994 | Liebl et al. | |
| 5,312,355 A | 5/1994 | Lee | |
| 5,312,357 A | 5/1994 | Buijs et al. | |
| 5,320,602 A | 6/1994 | Karpiel | |
| 5,324,271 A | 6/1994 | Abiuso et al. | |
| 5,334,157 A | 8/1994 | Klein et al. | |
| 5,334,187 A | 8/1994 | Fischell et al. | |
| 5,336,192 A | 8/1994 | Palestrant | |
| 5,348,537 A | 9/1994 | Wiesner et al. | |
| 5,350,362 A | 9/1994 | Stouder, Jr. | |
| 5,350,363 A | 9/1994 | Goode et al. | |
| 5,360,403 A * | 11/1994 | Mische | 604/101.02 |
| 5,364,393 A | 11/1994 | Auth et al. | |
| 5,368,574 A | 11/1994 | Antonacci et al. | |
| 5,382,241 A | 1/1995 | Choudhury et al. | |
| 5,389,090 A | 2/1995 | Fischell et al. | |
| 5,391,152 A | 2/1995 | Patterson | |
| 5,395,352 A | 3/1995 | Penny | |
| 5,397,311 A | 3/1995 | Walker et al. | |
| 5,405,320 A | 4/1995 | Twardowski et al. | |
| 5,405,323 A | 4/1995 | Rogers et al. | |
| 5,409,463 A | 4/1995 | Thomas et al. | |
| 5,409,464 A | 4/1995 | Villalobos | |
| 5,409,469 A | 4/1995 | Schaerf | |
| 5,413,561 A | 5/1995 | Fischell et al. | |
| 5,419,340 A | 5/1995 | Stevens | |
| 5,423,762 A | 6/1995 | Hillstead | |
| 5,429,616 A | 7/1995 | Schaffer | |
| 5,437,645 A | 8/1995 | Urban et al. | |
| 5,441,504 A | 8/1995 | Pohndorf et al. | |
| 5,445,613 A * | 8/1995 | Orth | 604/66 |
| 5,453,095 A | 9/1995 | Davila et al. | |
| 5,460,616 A | 10/1995 | Weinstein et al. | |
| 5,472,418 A | 12/1995 | Palestrant | |
| 5,472,435 A | 12/1995 | Sutton | |
| 5,474,099 A | 12/1995 | Boehmer et al. | |
| 5,484,401 A | 1/1996 | Rodriguez | |
| 5,488,960 A | 2/1996 | Toner | |
| 5,496,346 A | 3/1996 | Horzewski et al. | |
| 5,501,676 A | 3/1996 | Niedospial et al. | |
| 5,509,897 A | 4/1996 | Twardowski et al. | |
| 5,520,655 A | 5/1996 | Davila et al. | |
| 5,536,255 A | 7/1996 | Moss | |
| 5,538,505 A | 7/1996 | Weinstein et al. | |
| 5,599,305 A | 2/1997 | Hermann et al. | |
| 5,613,953 A | 3/1997 | Pohndorf | |
| 5,613,956 A | 3/1997 | Patterson et al. | |
| 5,647,857 A | 7/1997 | Anderson et al. | |
| 5,653,698 A | 8/1997 | Niedospial et al. | |
| 5,672,158 A | 9/1997 | Okada et al. | |
| 5,685,856 A | 11/1997 | Lehrer | |
| 5,702,370 A | 12/1997 | Sylvanowicz et al. | |
| 5,713,867 A | 2/1998 | Morris | |
| 5,735,819 A | 4/1998 | Elliott | |
| 5,741,233 A | 4/1998 | Riddle et al. | |
| 5,752,937 A | 5/1998 | Otten et al. | |
| 5,755,693 A | 5/1998 | Walker et al. | |
| 5,755,702 A | 5/1998 | Hillstead et al. | |
| 5,766,203 A | 6/1998 | Imran et al. | |
| 5,772,678 A | 6/1998 | Thomason et al. | |
| 5,782,807 A | 7/1998 | Falvai et al. | |
| 5,782,817 A | 7/1998 | Franzel et al. | |
| 5,785,694 A * | 7/1998 | Cohen et al. | 604/250 |
| 5,800,414 A | 9/1998 | Cazal | |
| 5,853,393 A | 12/1998 | Bogert | |
| 5,858,007 A | 1/1999 | Fagan et al. | |
| 5,879,333 A | 3/1999 | Smith | |
| 5,885,217 A | 3/1999 | Gisselberg et al. | |

| | | | |
|---|---|---|---|
| 5,895,376 A * | 4/1999 | Schwartz et al. | 604/256 |
| 5,911,710 A | 6/1999 | Barry et al. | |
| 5,916,194 A | 6/1999 | Jacobsen et al. | |
| 5,919,160 A | 7/1999 | Sanfilippo, II | |
| 5,921,968 A | 7/1999 | Lampropoulos et al. | |
| 5,935,112 A | 8/1999 | Stevens et al. | |
| 5,944,695 A | 8/1999 | Johnson et al. | |
| 5,951,518 A | 9/1999 | Licata et al. | |
| 5,957,912 A | 9/1999 | Heitzmann | |
| 5,967,490 A | 10/1999 | Pike | |
| 5,971,958 A | 10/1999 | Zhang | |
| 6,024,729 A | 2/2000 | Dehdashtian et al. | |
| 6,027,480 A | 2/2000 | Davis et al. | |
| 6,033,375 A | 3/2000 | Brumbach | |
| 6,033,388 A | 3/2000 | Nordstrom et al. | |
| 6,053,904 A | 4/2000 | Scribner et al. | |
| 6,074,377 A | 6/2000 | Sanfilippo, II | |
| 6,083,207 A | 7/2000 | Heck | |
| 6,086,570 A | 7/2000 | Aboul-Hosn et al. | |
| 6,088,889 A | 7/2000 | Luther et al. | |
| 6,090,083 A * | 7/2000 | Sell et al. | 604/249 |
| 6,106,540 A | 8/2000 | White et al. | |
| 6,120,476 A | 9/2000 | Fung et al. | |
| 6,120,480 A | 9/2000 | Zhang et al. | |
| 6,142,981 A | 11/2000 | Heck et al. | |
| 6,159,198 A | 12/2000 | Gardeski et al. | |
| 6,162,196 A | 12/2000 | Hart et al. | |
| 6,171,281 B1 | 1/2001 | Zhang | |
| 6,179,806 B1 * | 1/2001 | Sansoucy | 604/30 |
| 6,210,366 B1 | 4/2001 | Sanfilippo, II | |
| 6,213,988 B1 | 4/2001 | McIvor et al. | |
| 6,221,057 B1 | 4/2001 | Schwartz et al. | |
| 6,228,060 B1 * | 5/2001 | Howell | 604/167.04 |
| 6,228,062 B1 | 5/2001 | Howell et al. | |
| 6,258,058 B1 | 7/2001 | Sanfilippo, II | |
| 6,273,871 B1 | 8/2001 | Davis et al. | |
| 6,276,661 B1 | 8/2001 | Laird | |
| 6,322,541 B1 | 11/2001 | West et al. | |
| 6,331,176 B1 | 12/2001 | Becker et al. | |
| 6,338,725 B1 | 1/2002 | Hermann et al. | |
| 6,352,520 B1 | 3/2002 | Miyazaki | |
| 6,402,723 B1 | 6/2002 | Lampropoulos et al. | |
| 6,413,250 B1 | 7/2002 | Smith | |
| 6,454,744 B1 | 9/2002 | Spohn et al. | |
| 6,458,103 B1 | 10/2002 | Albert et al. | |
| 6,494,860 B1 | 12/2002 | Rocamora et al. | |
| 6,497,681 B1 | 12/2002 | Brenner | |
| 6,508,790 B1 | 1/2003 | Lawrence | |
| 6,520,939 B1 | 2/2003 | Lafontaine | |
| 6,544,247 B1 | 4/2003 | Gardeski et al. | |
| 6,551,283 B1 | 4/2003 | Guo et al. | |
| 6,575,960 B1 | 6/2003 | Becker et al. | |
| 6,589,262 B1 | 7/2003 | Honebrink et al. | |
| 6,592,544 B1 | 7/2003 | Mooney et al. | |
| 6,623,460 B1 | 9/2003 | Heck | |
| 6,629,350 B1 * | 10/2003 | Motsenbocker | 29/283.5 |
| 6,632,200 B1 | 10/2003 | Guo et al. | |
| 6,638,242 B1 | 10/2003 | Wilson et al. | |
| 6,645,178 B1 | 11/2003 | Junker et al. | |
| 6,663,595 B1 | 12/2003 | Spohn et al. | |
| 6,682,498 B1 | 1/2004 | Ross | |
| 6,682,519 B1 | 1/2004 | Schon | |
| 6,689,109 B1 * | 2/2004 | Lynn | 604/250 |
| 6,692,464 B1 | 2/2004 | Graf | |
| 6,695,832 B1 | 2/2004 | Schon et al. | |
| 6,712,796 B1 * | 3/2004 | Fentis et al. | 604/247 |
| 6,719,749 B1 | 4/2004 | Schweikert et al. | |
| 6,827,710 B1 | 12/2004 | Mooney et al. | |
| 6,872,198 B1 | 3/2005 | Wilson et al. | |
| 6,881,211 B1 | 4/2005 | Schweikert et al. | |
| 6,887,220 B1 * | 5/2005 | Hogendijk | 604/119 |
| 6,916,313 B1 | 7/2005 | Cunningham | |
| 2001/0041873 A1 | 11/2001 | Dopper et al. | |
| 2002/0077605 A1 * | 6/2002 | Fentis et al. | 604/247 |
| 2002/0099327 A1 * | 7/2002 | Wilson et al. | 604/43 |
| 2003/0225379 A1 * | 12/2003 | Schaffer et al. | 604/250 |
| 2004/0065333 A1 | 4/2004 | Wilson et al. | |
| 2004/0092863 A1 | 5/2004 | Raulerson et al. | |
| 2004/0097903 A1 | 5/2004 | Raulerson | |
| 2004/0122418 A1 | 6/2004 | Voorhees | |
| 2004/0158208 A1 | 8/2004 | Hiejima | |
| 2004/0167478 A1 | 8/2004 | Mooney et al. | |
| 2004/0171997 A1 | 9/2004 | Wilson et al. | |
| 2004/0172003 A1 | 9/2004 | Wilson et al. | |
| 2004/0176739 A1 | 9/2004 | Stephens et al. | |
| 2004/0186444 A1 | 9/2004 | Daly et al. | |
| 2004/0186445 A1 * | 9/2004 | Raulerson et al. | 604/250 |
| 2004/0193119 A1 | 9/2004 | Canaud et al. | |
| 2004/0243095 A1 | 12/2004 | Nimkar et al. | |
| 2005/0049555 A1 | 3/2005 | Moorehead et al. | |
| 2005/0113805 A1 | 5/2005 | Devellian et al. | |
| 2006/0015074 A1 * | 1/2006 | Lynn | 604/250 |

FOREIGN PATENT DOCUMENTS

| | | |
|---|---|---|
| EP | 1240916 A1 | 9/2002 |
| WO | WO 97/22374 | 6/1997 |
| WO | WO 00/23137 | 4/2000 |

OTHER PUBLICATIONS

*Health Devices* May-Jun. 1996: 25(5-6):214-5.

Camp, "Care of the Groshong Catheter", Oncol Nurs Forum, vol. 15, No. 6, 1988.

Delmore et al., "Experience with the Groshong Long-Term Central Venous Catheter", Gynecologic Oncology 34, 216-218 (1989).

Malviya et al., "Vascular Access in Gynecological Cancer Using the Groshong Right Atrial Catheter", Gynecological Oncology 33, 313-316 (1989).

* cited by examiner

VALVED CATHETER

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

FIELD OF INVENTION

The present invention is generally in the field of medical devices. More particularly, the present invention relates to a valved catheter that allows placement and withdrawal of an accessing device or attachable unit without the risk of air embolism or blood loss.

BACKGROUND OF THE INVENTION

There are a variety of conditions that require injection of fluids into, or withdrawing fluids from, parts of a body below the surface of the skin of the body. During the procedure, symptomatic gas embolism can occur when undissolved gas (e.g., air, $CO_2$) accumulates in the heart and/or pulmonary arteries. This gas can compromise the circulation of blood through the lungs, causing serious injury or death.

Health Devices May–June 1996; 25(5–6):214-5 reported a case of suspected gas embolism. During a hysteroscopy (performed with a patient under intravenous sedation), the patient gasped for air almost immediately upon uterine insufflation. Based on the clinical signs, the medical staff suspected that the patient's condition was caused by a $CO_2$ embolism that originated in the uterus. However, a follow up investigation revealed that the embolized gas was probably air, not $CO_2$. The air may have been introduced into the patient from the dead space in the tubing set used to connect the insufflator to the hysteroscope. This tubing set was not purged before insufflation began. Health Devices recommended that before delivering a fluid to a patient, one must purge air from tubing sets and instruments. Thus, there is a need for a valved catheter wherein the valved catheter comprises a safety valve having substantially zero dead space built-in the catheter tube that would automatically close to reduce the risk of blood loss or air embolism if an attachment to the catheter were to be inadvertently disconnected from the catheter tube.

It is common to use an implanted catheter to repeatedly access the vascular system of a patient. A flexible guidewire placed in the vascular system can be used to facilitate placement of the catheter, but its use can prevent capping the catheter to prevent fluid loss from or air entering the vascular system during placement. After catheter placement, it is common to attach a valved cap to the catheter connector(s) to prevent fluid loss from or air entering the catheter and vascular system. U.S. Pat. No. 6,575,960 (Bleed Back Control Assembly and Method) relates to a Y-valved connector. The 'Y-connector' includes a sealing valve that is normally closed except when accessed with a small diameter tube or wire. The sealing valve does not completely prevent air or fluid leakage, but relies on a second user compressible valve to provide a complete seal.

In short, there are several problems with the current valves. The flow path through the valve is restricted due to a restricted cross-sectional area. There is a dead space above or below the valve where blood accumulates, which makes it difficult to clean the valve. The current valves are not designed for use with a guidewire traversing through the same valve. Also, the valves cannot be accessed multiple times; they are typically screwed on to the catheter and discarded after use.

Therefore, there is a need for a valved catheter that solves the above-mentioned problems and thereby reduces the risk of contamination and permits repeated use of the valved catheter for the life of the catheter which could be on the order of several years.

SUMMARY OF THE INVENTION

Accordingly, a valved catheter is described herein that has an integral valve system intended to remain patent for the life of the catheter, which could be several years. During the life of the catheter, the valve should maintain functionality to provide multiple functions, such as, for example: (a) sealing off the open end of the catheter during placement into the vein, (b) sealing the catheter tube except when being accessed by an accessing device, such as a syringe or guidewire, to prevent blood loss or air embolism, (c) providing unobstructed flow to a fluid from an attachable unit, such as a bifurcation fitting, when attached to the catheter, (d) providing a safety valve with substantially zero dead space that automatically closes if the accessing device or attachable unit is disconnected from the catheter, to prevent blood loss or air embolism, and (e) providing for an "over the guidewire" placement or replacement technique. In addition, it should be appreciated that other advantageous functions would be provided by the valved catheter of the present invention.

In one embodiment of the present invention a valved catheter comprises a catheter tube and a compression sleeve, said catheter tube comprising at least one lumen and having a necked portion formed in a proximal end thereof, said compression sleeve being positioned around said necked portion, wherein said at least one lumen is biased in a closed position at said necked portion by said compression sleeve, and wherein said at least one lumen assumes an open position when an attachable unit or accessing device is inserted through said necked portion

BRIEF DESCRIPTION OF THE DRAWINGS

In the accompanying drawings, reference characters refer to the same parts throughout the different views. The drawings are intended for illustrating some of the principles of providing a valved catheter and are not intended to limit the description in any way. The drawings are not necessarily to scale, emphasis instead being placed upon illustrating the depicted principles in a clear manner.

DETAILED DESCRIPTION OF THE INVENTION

Figure 1:
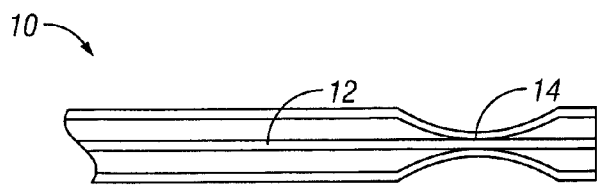
FIG. 1 is a cross-sectional view of a catheter tube in isolation with opposing sides thereof at a necked portion shown compressed to meet a septum.

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

A valved catheter design that allows placement of attachable catheters (single or multiple lumen) without risk of air embolism or blood loss through the open (proximal) end of the catheter tube. The valved design allows passage of a standard guidewire for 'over the guidewire' placement. The design prevents blood loss or air embolism from occurring if the catheter becomes detached from an attachable unit and when an accessing device is withdrawn therefrom. The valved catheter includes a catheter tube having a necked portion in its proximal end that forms an integral valve, the necked portion being surrounded by a compression sleeve that biases the valve in a closed position. In one embodiment, the compression sleeve incorporates a compression wedge and a compression ring to improve valve closure. The valved catheter may be accessed by inserting a rigid stem(s) into the tube and through the valved area, permitting unimpeded flow through the catheter.

As stated, the valved catheter has an integral valve system. The catheter can be a single or multi-lumen configuration and can be made of any suitable material, such as silicone or polyurethane, for example. The valve seals the catheter tube except when being accessed by an accessing device, such as a syringe (for infusion or aspiration) or a guidewire, or an attachable unit, such as an attachable bifurcation. One of the purposes of the valve is to seal off the proximal end of the catheter during placement into the vein. This prevents blood loss or air embolism that may occur if the catheter end is open, as in the case for attachable catheters. With a syringe attached thereto, the catheter may be infused (flushed with saline) or aspirated to verify blood flow through the catheter. By utilizing the valved catheter according to the present invention, adapters and clamps are unnecessary.

Another design feature of the valved catheter of the present invention provides unobstructed flow to a fluid from an attachable unit, such as an attachable bifurcation, when attached to the catheter. Yet another design feature of the valved catheter of the present invention provides a safety valve with substantially zero dead space that automatically closes if an accessing device or attachable unit is disconnected, in order to prevent blood loss or air embolism. Another design feature of the valved catheter of the present invention provides for passage of a guidewire through the catheter and attachable bifurcation. The guidewire can be inserted into the catheter tip (distal end) and passed through the guidewire guide in the valve of the valved catheter to guide the guidewire through the valve and through the multifunction adaptor assembly. Passing the guidewire through the valve minimizes risks associated with blood loss and/or air embolisms possible in an open end catheter design.

Figure 2:
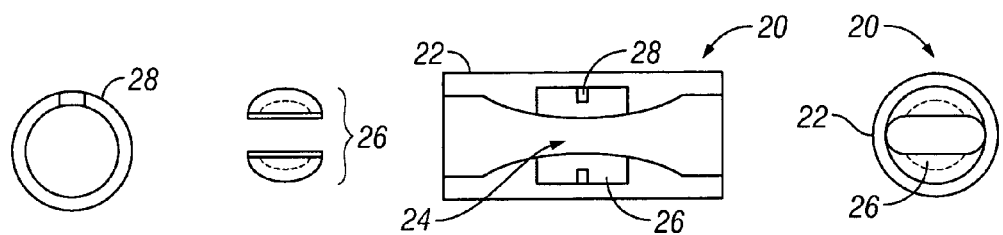
FIG. 2 are selected views of a compression sleeve and components thereof according to the present invention.
Figure 3:
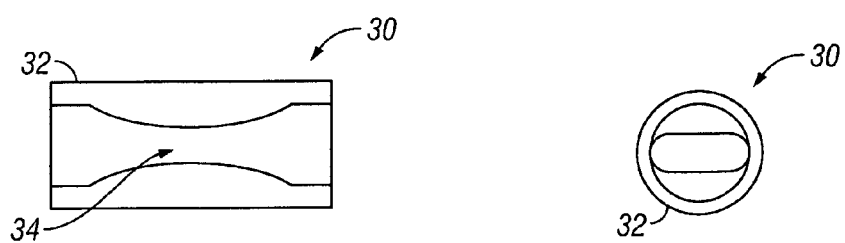
FIG. 3 includes a cross-sectional view and an end view of a compression sleeve according to the present invention.

FIGS. 1–3 illustrate separate components of a valved catheter according to the present invention. FIG. 1 illustrates a cross-section of a catheter tube 10 having a dual lumen configuration wherein separate lumens are divided by a septum 12, shown in a closed position with opposing sides of the tube 10 meeting at the septum. It should be noted that the present invention can equally be applied to a single lumen catheter or a catheter having more than two lumens. The catheter tube 10, preferably made of soft material, such as silicone or low durometer polyurethane is thermoformed or compression molded to form a necked portion 14 at the proximal end thereof. The necked portion 14 is formed, such that the outer wall of the catheter tube 10 on opposing sides thereof are compressed by a compression sleeve to meet the septum 12, effectively closing the lumens to air and fluid as explained below. It is important that the material for the catheter tube 10 be relatively soft (preferably with a hardness of 40 (or lower) to 60 Shore A) such that the force required to ensure closure thereof at the necked portion 14 is not so high that certain accessing devices would be precluded from use therewith.

FIG. 2 shows one embodiment of a compression sleeve according to the present invention, which is designed to be positioned around the necked portion 14 of the catheter tube 10 to ensure that the necked portion 14 closes for the life of the catheter tube 10 during implantation and when accessing devices or attachable units are withdrawn following insertion therethrough. Compression sleeve 20 includes a sleeve portion 22, which is formed to have a central passage for receiving the catheter tube 10, the central passage having a necked portion 24 fashioned to receive necked portion 14 of the catheter tube 10. Positioned around the necked portion 24 is a compression wedge 26 into which is formed a split compression ring 28. The split compression ring 28 could be composed of spring steel and could be an overlapping ring design with split open ends to allow ring expansion when the valve is accessed and to facilitate valve closure when the accessing device is withdrawn. Of course, one of skill in the art would recognize that there are many other mechanical spring assisted closing devices that could also be used, which would equally be within the scope of the present invention. In addition, many materials are possible for the compression ring 28, including various metals and polymers. Together, the compression wedge 26 and the compression ring 28 provide the compression sleeve 20 with an inwardly directed force to ensure closure of the necked portion 14 of catheter tube 10 when placed therearound. It should be noted that in the preferred embodiment, the compression sleeve 20 is configured for permanent attachment to catheter tube 10.

FIG. 3 illustrates another embodiment of a compression sleeve according to the present invention. Compression sleeve 30 includes a sleeve portion 32, which is formed to have a central passage for receiving the catheter tube 10, the central passage having a necked portion 34 fashioned to receive the necked portion 14 of the catheter tube 10. Compression sleeve 30 is preferably made from a silicone material with resilient properties such that necked portion 34 will assume its original shape following removal of a previously inserted accessing device or attachable unit into the necked portion 14 of the catheter tube 10. Preferably, compression sleeve 30 is made from a material having a hardness higher than that of the catheter tube 10. Thus, for example, a very soft catheter tube (e.g., 40 Shore A or less) would require a compression sleeve having a hardness in the range of approximately 50 to 60 Shore A for proper functioning, while a catheter tube having a hardness of 60 Shore A or higher would require a compression sleeve having a hardness of approximately 70 Shore A or higher. Of course, these values hold true for a compression sleeve that is only slightly larger than the catheter tube, which is the preferred configuration of the present invention to meet the goals of facilitated placement and patient comfort. However, also contemplated are compression sleeves that have much larger diameters than the catheter tube, in which case as the diameter of the compression sleeve increases, the required hardness of the material generally decreases.

Figure 4:
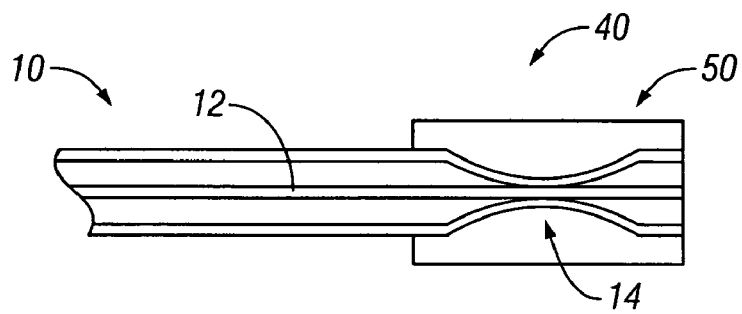
FIG. 4 is a cross-sectional view of a proximal end of a valved catheter according to the present invention.

FIG. 4 illustrates a valved catheter 40, wherein a compression sleeve 50 is permanently affixed to the proximal end of the catheter tube 10. Compression sleeve 50 could be formed according to compression sleeves 20 or 30, or the like, the primary consideration being that compression sleeve 50 provides an inwardly directed force to the necked portion 14 such that in the absence of an accessing device or attachable unit inserted therethrough, the necked portion 14 remains tightly situated against septum 12. As mentioned above, such a configuration prohibits the passage of air or fluid through the necked portion 14, which is advantageous in placing catheter 10 into a body lumen, as well as maintaining the position of the catheter 10 once placed when it is desired to change or alternate accessing devices or attachable units. Of course, in the case of a single lumen design, the necked portion 14 would be tightly situated against itself (i.e., the opposing walls of the catheter would be in contact), and in the case of a design having more than two lumens, the necked portion would be tightly situated against perhaps more than one septum.

Figure 5:
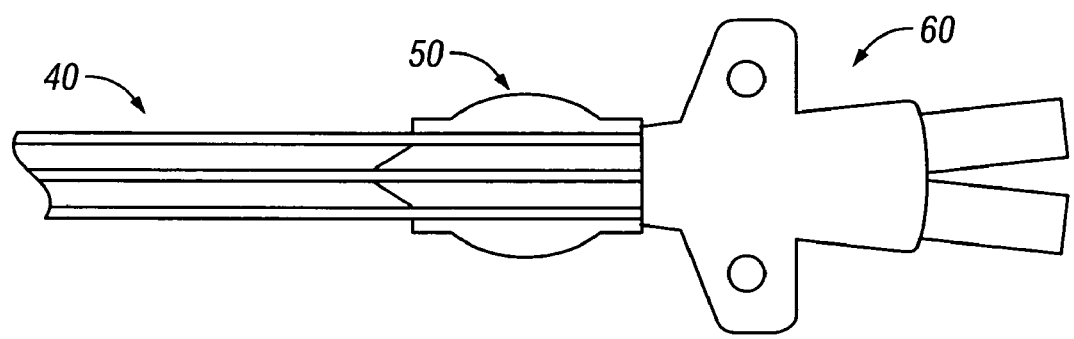
FIG. 5 is a cross-sectional view of an attachable bifurcation inserted into the proximal end of the valved catheter of FIG. 4.

FIG. 5 illustrates an attachable unit inserted into valved catheter 40, the attachable unit in this instance being an attachable bifurcation 60. When the attachable bifurcation 60, or any other attachable unit, is attached to the valved catheter 40, the flow of a fluid from the attachable bifurcation 60 into the catheter tube 10 is unobstructed by any restrictor such as a pinched or reduced opening. On the other hand, when the attachable bifurcation 60 is separated from the valved catheter 40, the valved catheter 40 automatically shuts off the flow of air or fluid therethrough due to the auto closure feature thereof, resulting from the pinching at the necked portion 14 of the catheter tube 10 by the compression sleeve 50. The valved catheter 40 without the attachable bifurcation 60 or other attachable unit or accessing device would remain closed at the necked portion 14 to prevent the flow of a fluid or air past the necked portion 14 under normal body pressure (both positive and negative), which, for example, could be approximately 1 psig (positive or negative) or less. In different embodiments, the valved catheter could be designed to allow the flow of a fluid past the necked portion at a fluid pressure of about ¼, ½, ¾ or 1 psig or higher (positive or negative).

In a preferred embodiment, the valved catheter 40 is designed to have a high enough compression to seal above pressures (positive and negative) that are normally seen in the venous side of the circulatory system, but not so high of a compression such that it would be difficult or impossible to (a) pass a standard floppy tip guidewire therethrough, or (b) aspirate or infuse therethrough. In one embodiment, the catheter tube 10 is made of a polyurethane material having a hardness in the range of approximately 70–75 Shore A, while the compression sleeve 50 is made of a silicone material having a hardness of approximately 80 Shore A.

The valved catheter 40 may be designed to be small enough to fit within a cylindrical housing with dimensions of 0.25 inch diameter or smaller and 1.0 inch length or less to facilitate passage through a subcutaneous tunnel. A subcutaneously tunneled catheter is often selected when a catheter might be required to be implanted within a patient for weeks to months. A subcutaneously tunneled catheter can be implanted or removed in the outpatient setting and has a decreased incidence of infection. The typical procedure for implanting the tunneled catheter is by forward tunneling. However, a more preferred method of implanting the tunneled catheter is by reverse tunneling as follows: (a) place the distal end of the catheter within the blood vessel through an entry site; (b) mark an exit locations of a tunnel to be formed in a subcutaneous plane; (c) create the subcutaneous tunnel from the exit to entry site using a tunneler by pushing the sharp point of the tunneler through the skin; (d) attach the proximal end of the catheter to the sharp point of the tunneler; (e) pull the tunneler with the secured catheter from the entry to the exit site, through the subcutaneous tunnel, while gently holding the catheter distal to the cuff; and (f) detach the catheter from the tunneler and attach a bifurcation element thereto. During the described reverse tunneling technique, the proximal end of a typical catheter tube is open, permitting the entry of air. If the proximal end is clamped, the catheter cannot be reverse tunneled as described. Thus, the valved catheter 40 is advantageous for its use in reverse tunneling without the risk of air embolism.

The valved catheter of the present invention may be designed for incorporation within a small housing that is compatible with multiple fittings, i.e., luer lock, slip fit, compression, etc. Valve function or performance is not affected by the addition of color or clear housing/components. Component or housing components are not affected by opacity or color. Markings and scales could be used on an as needed basis per application. Device function is not integrally linked to markings, etc. Device is sterilizable using standard techniques (EtO, gamma, etc.). The methods of manufacturing the valved catheter of the different embodiments include machining or molding/forming the components of the catheter tube and compression sleeve. While the device is primarily contemplated for use in human patients, the invention will also have veterinary uses or product development purposes in equine, bovine, canine, feline, and other mammalian species.

The present invention has been described above in terms of certain preferred embodiments so that an understanding of the present invention can be conveyed. However, there are many alternative arrangements not specifically described herein, but with which the present invention is applicable. Although specific features have been provided, the present invention would equally be embodied by other configurations not specifically recited herein. The scope of the present invention should therefore not be limited by the embodiments illustrated, but rather it should be understood that the present invention has wide applicability with respect to catheter systems generally. All modifications, variations, or equivalent elements and implementations that are within the scope of the appended claims should therefore be considered within the scope of the invention.

The invention claimed is:

1. A valved catheter, comprising a catheter tube and a compression sleeve, said catheter tube comprising a first lumen separated from a second lumen by a septum, the catheter tube having a necked portion formed along a proximal section, said compression sleeve being positioned around said necked portion, to bias the first lumen and second lumen in a closed position.

2. The valved catheter according to claim 1, further comprising an attachable bifurcation.

3. The valved catheter according to claim 1, wherein said compression sleeve comprises a compression ring and a compression wedge.

4. The valved catheter according to claim 3, wherein said compression ring is made of a metal, polymer or spring steel material.

5. The valved catheter according to claim 1, wherein said compression sleeve is made of silicone.

6. The valved catheter according to claim 1, wherein said compression sleeve is made from a material that has a hardness in the range of approximately 50 to 80 Shore A, and wherein said catheter tube is made from a material that has a hardness in the range of approximately 40 to 60 Shore A.

7. The valved catheter according to claim 1, wherein said compression sleeve is made from a material that has a hardness in the range of approximately 70 to 100 Shore A, and wherein said catheter tube is made from a material that has a hardness in the range of approximately 60 to 80 Shore A.

8. The valved catheter according to claim 7, wherein said compression sleeve is made from a silicone material that has a hardness of approximately 80 Shore A, and wherein said catheter tube is made from a polyurethane material that has a hardness in the range of approximately 70 to 75 Shore A.

9. A catheter, comprising:
   a catheter tube, including a first lumen separated along a length of the catheter tube from a second lumen by a septum, and a necked portion along a proximal section of the catheter tube; and
   a compression sleeve positioned about the necked portion, including a reduced diameter section that directs a force against the first lumen and second lumen, to bias the first lumen and second lumen in a closed position.

10. The catheter according to claim 9, wherein the material of the compression sleeve is resilient such that following removal of an inserted accessing device, the compression sleeve assumes its original shape.

11. The catheter according to claim 9, wherein the compression sleeve comprises a compression wedge including a split compression ring.

12. The catheter according to claim 9, wherein the width of the septum along the necked portion section is less than the width of the septum along an adjacent section of the catheter tube.

13. The catheter according to claim 9, wherein the compression sleeve has a material hardness harder than a material hardness of the catheter tube.

14. The catheter according to claim 9, wherein the compression sleeve has a material hardness in the range of approximately 50 Shore A to approximately 80 Shore A, and wherein the catheter tube has a material hardness in the range of approximately 40 Shore A to approximately 60 Shore A.

15. A catheter assembly, comprising:
   a catheter tube, including a first lumen separated from a second lumen by a septum and a necked portion positioned in a proximal end of the catheter tube;
   a compression sleeve positioned about the necked portion to bias the first lumen and second lumen in a closed position; and
   an attachable bifurcation having a portion configured for insertion into the first and second lumens such that upon attachment of the bifurcation to the catheter tube, the first and second lumens are open to fluid flow.

16. The catheter assembly according to claim 15, wherein the material of the compression sleeve is resilient such that following removal of the bifurcation, the compression sleeve assumes its original shape effectively closing the first and second lumens to the flow of air and fluid.

17. The catheter according to claim 15, wherein the width of the septum along the necked portion section is less than the width of the septum along an adjacent section of the catheter tube.

18. The catheter according to claim 15, wherein the compression sleeve has a material hardness harder than a material hardness of the catheter tube.

19. The catheter according to claim 15, wherein the compression sleeve has a material hardness in the range of approximately 50 Shore A to approximately 80 Shore A, and wherein the catheter tube has a material hardness in the range of approximately 40 Shore A to approximately 60 Shore A.

20. The catheter according to claim 15, wherein the catheter tube comprises silicone or low durometer polyurethane.

* * * * *